(12) United States Patent
Tuunanen

(10) Patent No.: US 6,207,463 B1
(45) Date of Patent: *Mar. 27, 2001

(54) SEPARATION DEVICE FOR MICROPARTICLES INVOLVING A MAGNETIC ROD

(75) Inventor: Jukka Tuunanen, Helsinki (FI)

(73) Assignee: Labsystems Oy, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 08/817,688
(22) PCT Filed: Oct. 20, 1995
(86) PCT No.: PCT/FI95/00577
§ 371 Date: Jun. 3, 1997
§ 102(e) Date: Jun. 3, 1997
(87) PCT Pub. No.: WO96/12958
PCT Pub. Date: May 2, 1996

(30) Foreign Application Priority Data

Oct. 20, 1994 (FI) .......................................... 944937

(51) Int. Cl.[7] ................... G01N 15/06; G01N 33/553; A01N 1/02; C12M 3/02
(52) U.S. Cl. ................... 436/526; 436/177; 436/806; 435/283.1; 435/287.1; 435/287.2; 210/222; 210/695; 294/65.5; 422/50; 422/68.1; 422/100; 422/101; 335/295
(58) Field of Search ................... 210/222, 695; 294/65.5; 335/295; 422/50, 68.1, 100, 101; 435/283.1, 287.1, 287.2; 436/526, 177, 806

(56) References Cited

U.S. PATENT DOCUMENTS

| 2,471,764 | 5/1949 | Miller et al. ............ 294/65.5 |
| 3,904,482 | 9/1975 | Mehl ..................... 195/109 |

(List continued on next page.)

FOREIGN PATENT DOCUMENTS

| 2824742 A1 | 2/1979 | (DE) . |
| 0027008 A1 | 4/1981 | (EP) . |
| 0186001 | 7/1986 | (EP) . |
| 0042755 B1 | 8/1988 | (EP) . |

(List continued on next page.)

Primary Examiner—Christopher L. Chin
Assistant Examiner—Pensee T. Do
(74) Attorney, Agent, or Firm—Fish & Richardson, P.C.

(57) ABSTRACT

The invention relates to a means for separating magnetic particles from a composition. The means comprises an elongated protective cover (1) that comprises a recess (2) extending from the upper end towards the lower end thereof, the recess comprising a movable magnetic rod (4), the proportion of the length of the rod to its thickness being at least about 2:1. The invention can be used in different applications especially in the fields of biotechnology, biochemistry, and biomedicine. Collecting particles by using the means is easy and fast.

13 Claims, 5 Drawing Sheets

U.S. PATENT DOCUMENTS

| | | | |
|---|---|---|---|
| 3,970,518 | 7/1976 | Giaever | 195/1.5 |
| 3,985,649 | 10/1976 | Eddelman . | |
| 4,018,886 | 4/1977 | Giaever | 424/12 |
| 4,115,535 | 9/1978 | Giaever | 424/1 |
| 4,200,613 | 4/1980 | Alfrey et al. | 422/71 |
| 4,272,510 | 6/1981 | Smith et al. | 427/47 |
| 4,438,068 | 3/1984 | Forrest | 422/61 |
| 4,495,151 | 1/1985 | Ohyama et al. | 422/102 |
| 4,649,116 | 3/1987 | Daty et al. . | |
| 4,731,337 | 3/1988 | Luotola et al. | 436/526 |
| 4,751,053 | 6/1988 | Dodin et al. . | |
| 4,891,321 | 1/1990 | Hubscher | 435/293 |
| 4,895,650 | 1/1990 | Wang | 210/222 |
| 5,167,926 | 12/1992 | Kimura et al. | 422/67 |
| 5,200,084 | 4/1993 | Liberti et al. | 210/695 |
| 5,206,034 | 4/1993 | Yamazaki | 425/145 |
| 5,318,914 | 6/1994 | Matte et al. | 436/526 |
| 5,466,574 | 11/1995 | Liberti et al. . | |
| 5,474,742 | 12/1995 | Tuuminen | 422/63 |
| 5,647,994 | 7/1997 | Tuuanen et al. | 210/695 |

FOREIGN PATENT DOCUMENTS

| | | |
|---|---|---|
| 0 317 286 | 5/1989 | (EP) . |
| 0 351 857 | 1/1990 | (EP) . |
| 0 358 948 | 3/1990 | (EP) . |
| 0 479 448 | 4/1992 | (EP) . |
| 0522322 | 1/1993 | (EP) . |
| 1414479 | 11/1975 | (GB) . |
| 2147 698 | 5/1985 | (GB) . |
| 2147898 | 5/1985 | (GB) . |
| 58-5656 | 1/1983 | (JP) . |
| 58-5657 | 1/1983 | (JP) . |
| 58-5658 | 1/1983 | (JP) . |
| 63-5263 | 1/1988 | (JP) . |
| 63-5265 | 1/1988 | (JP) . |
| 63-5266 | 1/1988 | (JP) . |
| WO 86/06493 | 11/1986 | (WO) . |
| WO 87/05536 | 9/1987 | (WO) . |
| WO 94/18565 | 8/1994 | (WO) . |
| WO 9418564 | 8/1994 | (WO) . |
| 95/00247 * | 1/1995 | (WO) . |
| WO 9612958 | 5/1996 | (WO) . |
| WO 9612959 | 5/1996 | (WO) . |
| WO 9612960 | 5/1996 | (WO) . |
| WO 9612961 | 5/1996 | (WO) . |

* cited by examiner

SEPARATION DEVICE FOR MICROPARTICLES INVOLVING A MAGNETIC ROD

TECHNICAL FIELD

The invention relates to the separation of magnetic particles from a composition. The invention can be used in different applications, especially in the fields of biotechnology, biochemistry, and biomedicine.

BACKGROUND OF THE INVENTION

Magnetic microparticles are used as a solid phase in various applications to bind biomaterial. One advantage of microparticles is the large area of the solid phase and short diffusion lengths. The size of microparticles is generally 0.05–10 μm and they are available in different materials and already activated for many applications. Magnetic particles can be moved by using a magnet.

The separation methods of magnetic particles currently used include settling a reaction vessel in a magnetic field so that particles are accumulated into a so-called pellet at the bottom of the vessel. Thereafter, the liquid which is free from particles is decanted or removed by aspiration. However, the removing of the liquid from the vessel must be carried out very carefully so as not to remove the particles at the same time.

Publication WO-86/06493 proposes a method to be used in immunoassays, in which magnetic particles and the marked complex adhered to them are separated from a liquid by using a magnetic rod and subsequently taken to be measured. The tip of the rod comprises a fixed magnet and a removable protective cover to whose outer surface the particles adhere. It is preferable to cover the protective cover with another cover after the separation and before measuring. After the measurement, the protective covers are detached together with the particles and thrown away and new covers are taken for a new separation. According to the publication, the magnet can also be an electromagnet, whereby the magnetic field can be eliminated when desired.

Publication WO-87/05536 proposes a device for separating magnetic particles, comprising, on the inside, a rod movable in a vertical boring and a magnet at the lower end thereof. The device is introduced, with the magnet in the lower position, into a liquid containing particles, whereby the particles are accumulated on the end of the rod. When the magnet is allowed into the upper position, the particles can be detached from the rod. In this way, particles can be collected and transferred from one liquid into another.

However, the disclosed separation devices and methods for magnetic particles cannot be applied very well in applications in which particles must be collected from a fairly large volume and transferred into an essentially smaller one.

SUMMARY OF THE INVENTION

Now, a separation method according to claim 1 has been invented. The other claims present some preferred embodiments of the invention.

The device according to the invention comprises an elongated protective cover that includes a movable rod comprising one rod magnet in the longitudinal direction of the cover. The proportion of the length of the rod magnet to its thickness is at least about 2:1, preferably at least about 3:1, and most preferably at least about 12:1. Both the intensity and the gradient of the magnetic field thus formed are the strongest at the end of the rod and when the magnet is in the lower position, the particles from the composition are accumulated directly on the tip of the cover. Particles can be released from the tip of the cover into a volume which is many times smaller than the original composition.

The rod magnet preferably consists of a permanent magnet and a ferromagnetic arm which is its extension.

The rod magnet is preferably sufficiently long so that the upper end of its dipole always remains above the surface of the composition. If particles are to be collected from a composition column higher than the dipole, it must be seen to that the particles from the upper part of the column are first collected on the tip so that the upper end of the dipole is constantly above the particles.

Since the upper end of the magnet can be above the composition, a more effective magnet with respect to the volume of the composition can be used, accelerating and facilitating the collection.

The device according to the invention comprises, in the tip of the protective cover, an intensive magnetic field in the direction of the cover. This is especially advantageous when particles are collected from a concentration of particles which has first been created in some other way. An additional advantage is that a high retaining strength can be provided directly in the tip from which the adhesion of the liquid particularly tends to detach particles when the protective cover is lifted off the liquid.

The tip of the protective cover is preferably provided with a sharp downward projection. This minimises the amount of liquid remaining in the tip. Typically, the tip is shaped like a cone. When transferring particles into very small vessels, the tip is preferably shaped as a cone with a concave surface.

When a ferromagnetic arm is used in the magnet, the magnet and the magnetised arm together function as a long rod magnet. The arm dissolves the gradient of the upper pole of the field, whereby the upper pole does not carry out the collection of particles. In this way, the long rod magnet can be provided at a low cost. However, even with a ferromagnetic arm, it is advantageous to use a relatively long magnet (with a length of about 1.5 . . . 10 times the thickness). The length of the magnet is preferably selected so that a maximum internal, permanent field intensity is provided for the magnet in question.

The junction between the magnet and its arm is preferably made so that the arm and the magnet come inside one another for a short length. In this way, the formation of strong gradients at the junction, which may possibly collect particles, is avoided.

The cross-section of the rod magnet can be, e.g., circular or rectangular. The circular shape is the best with respect to both manufacture and use. Indeed, the rotation of the magnet on its axis, for example, has no effect in this case. In principle, the rod can be curved to make the moving mechanisms simpler.

The shape of the protective cover on the rod can vary according to the use. Normally, the circular shape is the most advantageous with respect to both manufacture and use. In order to increase strength, the cover can be made conical, which also facilitates the manufacture of the cover by injection moulding. The cover is preferably made of polypropylene.

The invention is best-adapted to be used for particles of about 1–10μm.

BRIEF DESCRIPTION OF DRAWINGS

Some preferred applications of the invention are described in the following as examples. In the drawings of the description.

DETAILED DESCRIPTION OF THE INVENTION

Figure 1:
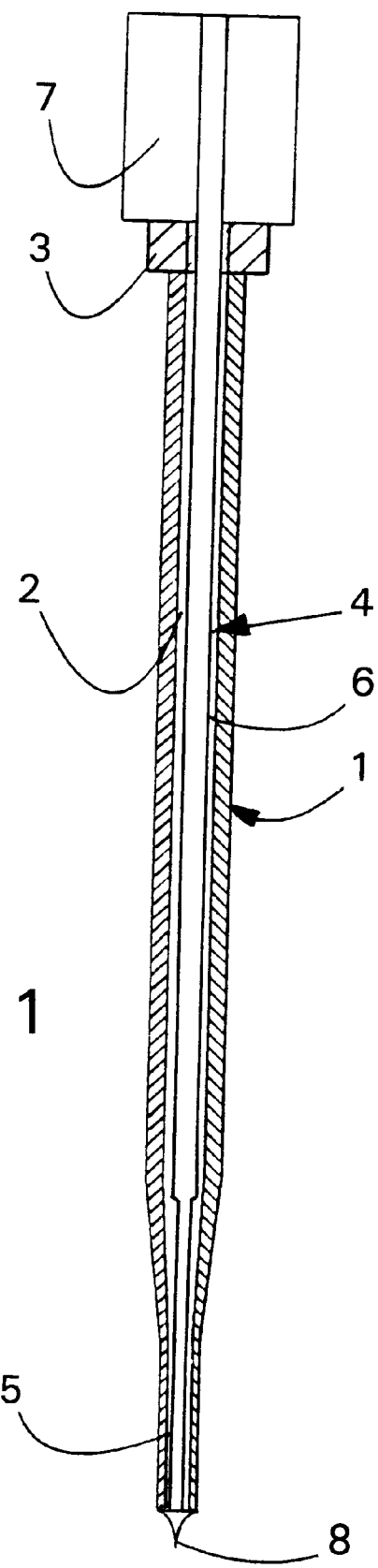
FIG. 1 presents a separation means according to the invention.

The separation rod according to FIG. 1 comprises an elongated protective cover 1 and a bore 2 in it. The lower ends of the cover and the bore are slightly tapered. The upper end of the body is provided with flange 3 which facilitates gripping.

Bore 2 comprises loose magnetic rod 4. This comprises vertical rod magnet 5 at the lower end thereof, and ferromagnetic arm 6 above it as an extension of the magnet. Gripping knob 7 is provided at the end of the arm.

The lower end of the cover is provided with a tapering, sharp-edged tip 8 with a concave surface. The length of the tip corresponds approximately to the width of the lower end of the cover.

Figure 2:
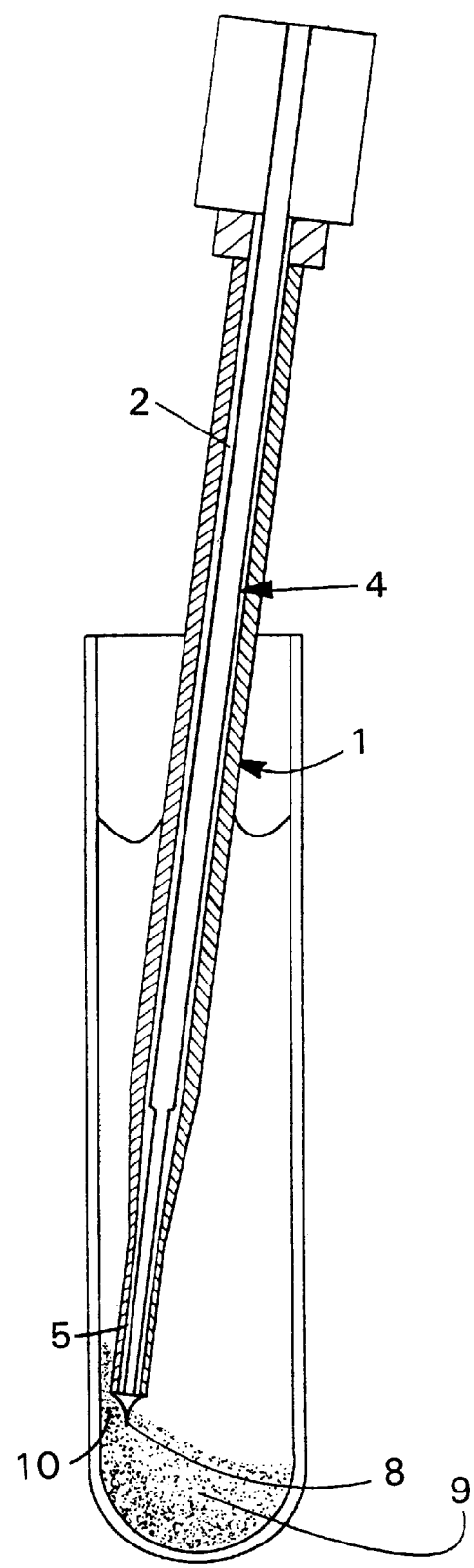
FIG. 2 presents the use of the means of FIG. 1 for collecting particles from a suspension.

FIG. 2 presents the collection of particles from a test tube where they are dispersed in suspension 9. The separation rod is moved in the test tube by sweeps up and down. In this way, particles can be collected at the tip to form an annular mass 10. When magnet 5 is kept in the lower end of bore 2, the particles remain attached to the tip. When particles are to be released, the magnet is lifted up.

Figure 3:
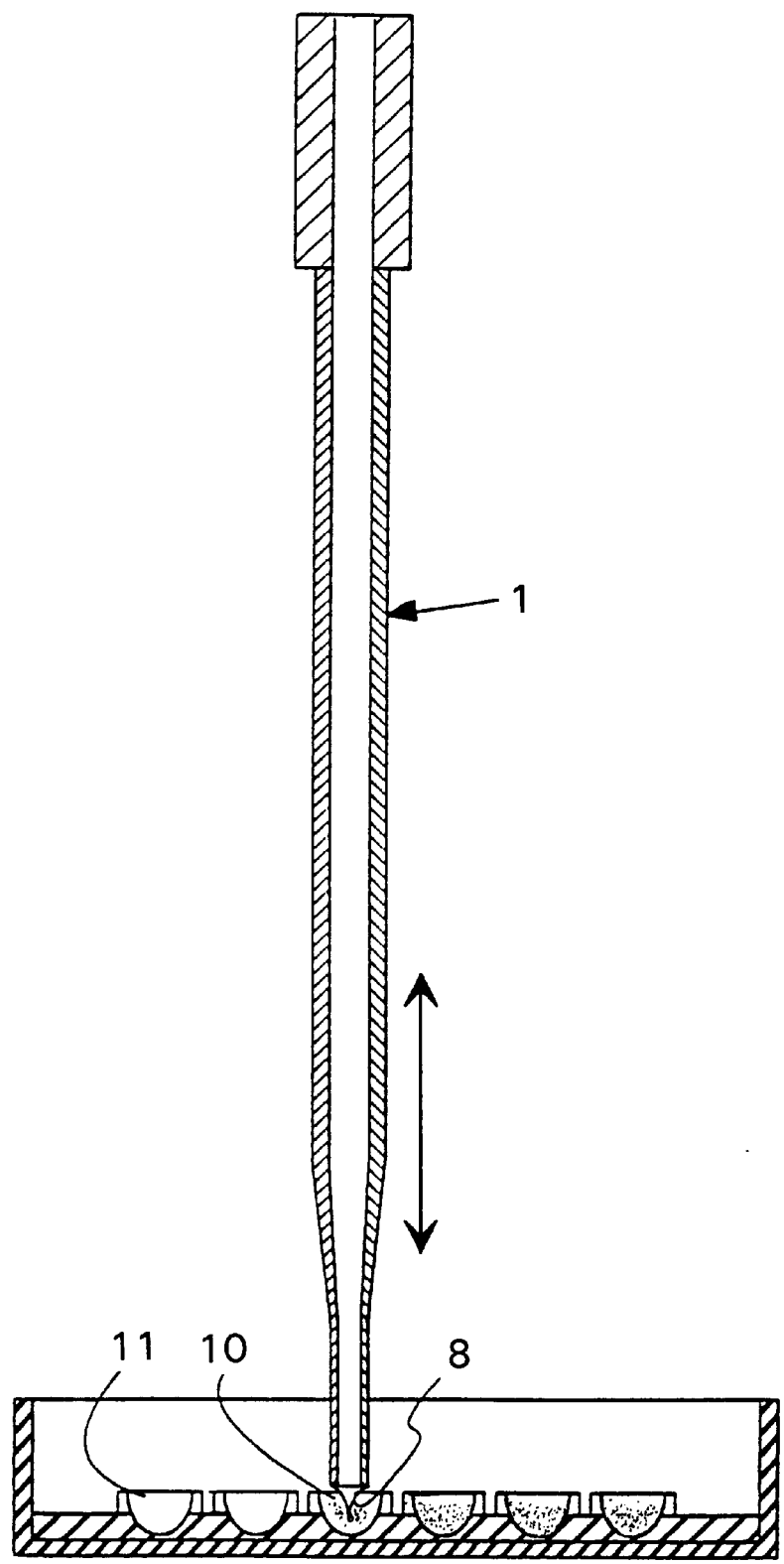
FIG. 3 presents the use of the means of FIG. 1 to release the collected particles into a very small vessel.

Tip 8 is especially well-adapted to transfer particles into a very small vessel, such as the well of a so-called HLA plate 11 (FIG. 3). The tip is slightly longer than the height of the well. When the tip is pushed into the well, the surface of the liquid rises along the surface of the tip due to surface tension. The edge of the moving surface of liquid sweeps the particles off the tip and into the liquid. The detachment can be improved by stirring the rod. Correspondingly, when the tip is lifted from the well, the surface of the liquid moves towards the sharp end of the tip as an integral film in this way, the liquid and the particles with it are completely detached from the tip.

The particles are preferably detached from the liquid so that they are first concentrated into one spot in the vessel from where they are then collected by using the rod. The concentration can be effected by letting the particles settle by gravitation, by centrifuging or by pulling the particles onto the wall of the vessel by using a magnetic field.

Figure 4:
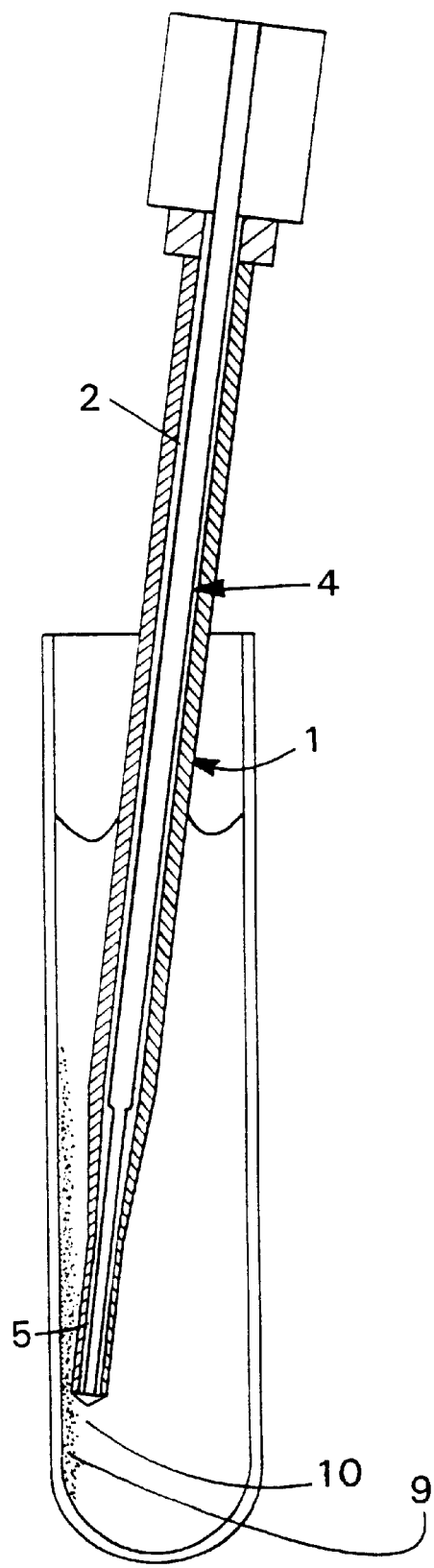
FIG. 4 presents the use of another means according to the invention for collecting particles from the wall of a test tube.

FIG. 4 presents the collection of particles from the wall of a test tube on which they were first pulled, by using a magnet, to form a vertical strip 9. By sweeping along the strip by the tip of the rod, the particles can be made to adhere to the tip of the protective cover 1 of the rod to form mass 10. Here the tip of protective cover 1 is shaped like a relatively blunt cone. This is well-adapted for transferring particles into vessels where the tip can be pushed properly into the liquid.

The proportion of the length of magnet 5 to the diameter is about 10:1, and the proportion of the length of the arm to the length of the magnet is about 5:1. The arm is slightly wider than the magnet and the upper end of the magnet is embedded inside the lower end of the arm at a length of about twice its diameter.

Figure 5:
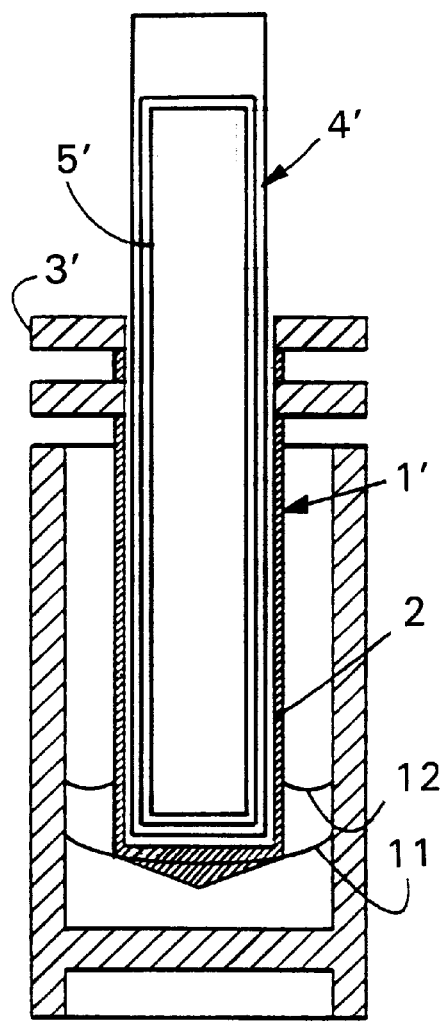
FIG. 5 presents the use of a third means according to the invention for collecting particles from a small amount of liquid.
Figure 6:
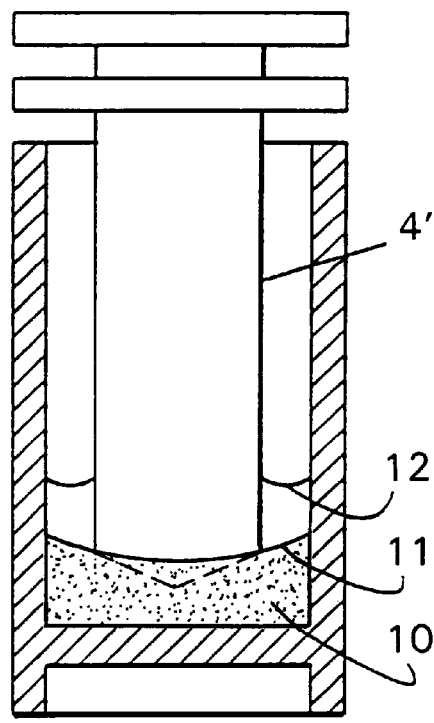
FIG. 6 presents the use of the means of FIG. 5 for releasing the collected particles into a small amount of liquid.

FIGS. 5 and 6 present a separation device including a magnetic rod 4' which comprises only a permanent magnet 5' coated with a suitable protective layer but no ferromagnetic arm. The upper end of protective cover 1' is provided with a gripping portion 3' with two flanges which enables the easy control of the device in automatic separation or analysis devices, for instance. The proportion of the length of the magnet to the diameter is about 7:1. The tip of the cover is shaped like a relatively blunt cone (the height of the cone being about ⅓ of its width).

FIG. 5 presents the separation of particles from a relatively narrow vessel compared with the separation rod (the inner diameter of the vessel is about 70% of the diameter of the rod) and from a relatively small amount of liquid. Lower line 11 presents the free surface of liquid and upper line 12 the surface of liquid when the separation means is pushed into the liquid. Magnetic particles are accumulated at the tip of the protective cover to form mass 10 which can be released back into a relatively small amount of liquid (FIG. 6).

The means of FIG. 5 and 6 is well-adapted to be used in the wells of microtitration plates with diameters of about 7 mm.

What is claimed is:

1. A means for separating magnetic particles from a composition, comprising:
   (a) a separation rod comprising a rod magnet including an elongated magnet at a lower end and a ferromagnetic arm attached to the elongated magnet; and
   (b) an elongated protective cover with a tip,
   wherein the resulting magnetic field is strongest at the lower end of the separation rod for accumulation of the particles from the composition on the tip of the protective cover, and wherein the protective cover covers the separation rod and is movable with respect to the rod, for release of the particles from the means for separating.

2. The means according to claim 1, wherein the proportion of the length of the rod magnet to its thickness is at least about 2:1.

3. The means according to claim 2, wherein the proportion of the length of the rod magnet to its thickness is at least about 3:1.

4. The means according to claim 2, wherein the proportion of the length of the rod magnet to its thickness is at least about 12:1.

5. The means according to claim 2, wherein the proportion of the length of the elongated magnet to its thickness is at least about 10:1 and the proportion of the length of the ferromagnetic arm to the length of the elongated magnet is about 5:1.

6. The means according to claim 2, wherein the ferromagnetic arm is thicker than the magnet and the upper end of the magnet is embedded inside the lower end of the ferromagnetic arm at a length of about twice the diameter of the magnet.

7. The means according to claim 2, wherein the tip of the protective cover is cone-shaped with a concave surface.

8. A method for separating magnetic particles from a liquid composition in a vessel, comprising:
   (a) providing a means for separating the magnetic particles, comprising:

(i) a separation rod comprising a rod magnet including an elongated magnet at a lower end and a ferromagnetic arm attached to the elongated magnet; and (ii) an elongated protective cover with a tip, wherein the resulting magnetic field is strongest at the lower end of the separation rod, and wherein the protective cover covers the separation rod and is movable with respect to the rod;

(b) placing the means for separating in the vessel containing the composition to accumulate the particles from the composition on the tip of the protective cover; and (c) removing the means for separating, along with the particles, from the vessel.

9. The method according to claim 8, wherein the means for separating is placed into the vessel such that an upper end of the long magnet remains above a surface of the liquid composition.

10. The method according to claim 8, further comprising releasing the particles from the means for separating into a further vessel by moving the protective cover with respect to the separation rod.

11. The method according to claim 8, wherein the proportion of the length of the elongated magnet to its thickness is at least about 2:1.

12. The method according to claim 11, wherein the proportion of the length of the elongated magnet to its thickness is at least about 3:1.

13. The method according to claim 12, wherein the proportion of the length of the elongated magnet to its thickness is at least 12:1.

* * * * *